United States Patent [19]

Laanio et al.

[11] 4,160,832
[45] Jul. 10, 1979

[54] NOVEL INSECTICIDES

[75] Inventors: Verena Laanio, Arisdorf; Hans U. Brechbühler, Basel; Dagmar Berrer, Riehen, all of Switzerland

[73] Assignee: Ciba-Geigy Corporation, Ardsley, N.Y.

[21] Appl. No.: 869,989

[22] Filed: Jan. 16, 1978

Related U.S. Application Data

[63] Continuation-in-part of Ser. No. 824,669, Aug. 15, 1977, abandoned.

[30] Foreign Application Priority Data

Aug. 19, 1976 [CH] Switzerland .................. 10559/76
Mar. 4, 1977 [CH] Switzerland .................. 2719/77

[51] Int. Cl.² .................. C07D 251/70; C07D 295/02; A61K 31/53; A61K 31/535
[52] U.S. Cl. .................. 424/248.56; 424/249; 544/113; 544/197; 544/198
[58] Field of Search .................. 544/197, 198, 113; 424/249, 248.56

[56] References Cited

U.S. PATENT DOCUMENTS

| 3,520,974 | 7/1970 | Hamm | 424/249 |
| 4,007,032 | 2/1977 | Berrer | 544/197 |
| 4,020,066 | 4/1977 | Bosshard et al. | 544/198 |

OTHER PUBLICATIONS

Borkovec et al., *J. of Medicinal Chem.*, vol. 10, pp. 457–461 (1967).

DeMilo et al., *J. of Medicinal Chem.*, vol. 11, pp. 961–963 (1968).

La Brecque et al., *J. Econ. Entomol.*, vol. 61, pp. 1621–1632 (1968).

*Primary Examiner*—John M. Ford
*Attorney, Agent, or Firm*—Harry Falber

[57] ABSTRACT

2-Cyclopropylamino-4-formylamino-6-amino-s-triazines of the formula

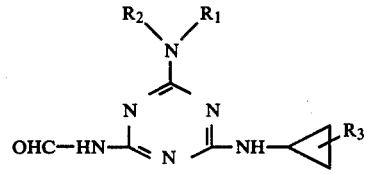

wherein
  $R_1$ represents hydrogen, $C_1$–$C_4$-alkyl which is unsubstituted or substituted by lower alkoxy, or represents $C_3$–$C_4$-alkenyl, $C_3$–$C_4$-alkynyl, cyclopropyl, hydroxy, methoxy or ethoxy,
  $R_2$ represents hydrogen, methyl or ethyl, or
  $R_1$ and $R_2$ together with the nitrogen atom to which they are attached represent a 5- or 6-membered heterocyclic ring which can contain a further nitrogen atom or an oxygen atom, and
  $R_3$ represents hydrogen or methyl,
and the acid addition salts thereof for combatting developmental stages of insects.

13 Claims, No Drawings

NOVEL INSECTICIDES

CROSS REFERENCE TO RELATED APPLICATION

This is a continuation-in-part of application Ser. No. 824,669, filed Aug. 15, 1977 now abandoned.

The present invention relates to novel 2-cyclopropylamino-4-formylamino-6-amino-s-triazine derivatives and salts thereof, to a process for their manufacture and to their use in pest control.

The 2-cyclopropylamino-4-formylamino-6-amino-s-triazine derivatives have the formula

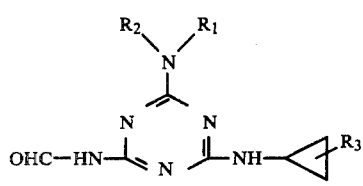

wherein $R_1$ represents hydrogen, $C_1$–$C_4$-alkyl which is unsubstituted or substituted by lower alkoxy, or represents $C_3$–$C_4$-alkenyl, $C_3$–$C_4$-alkynyl, cyclopropyl, hydroxy, methoxy or ethoxy, $R_2$ represents hydrogen, methyl or ethyl, or $R_1$ and $R_2$ together with the nitrogen atom to which they are attached represent a 5- or 6-membered heterocyclic ring which can contain a further nitrogen atom or an oxygen atom, and $R_3$ represents hydrogen or methyl, and the acid addition salts thereof.

Possible alkyl groups represented by $R_1$ can be straight-chain or branched, unsubstituted or substituted for example by alkoxy groups of 1 to 4 carbon atoms. Examples of such alkyl groups include methyl, ethyl, n-propyl, isopropyl, n-butyl, isobutyl, sec. and tert. butyl, and also 2-methoxyethyl. Examples of $C_3$–$C_4$-alkenyl and $C_3$–$C_4$-alkynyl groups comprise allyl and propargyl respectively.

The term "acid addition salts" of the 2-cyclopropylamino-4-formylamino-6-amino-s-triazine derivatives of the formula I is to be understood as meaning salts with strong mineral acids, for example salts with hydrochloric acid or sulphuric acid.

Preferred compounds on account of their action are compounds of the formula I in which $R_1$ represents hydrogen, $C_1$–$C_4$-alkyl which is unsubstituted or substituted by lower alkoxy, or represents $C_3$–$C_4$-alkenyl, $C_3$–$C_4$-alkynyl, cyclopropyl, hydroxyl, methoxy or ethoxy, $R_2$ represents hydrogen, methyl or ethyl, or $R_1$ and $R_2$ together with the nitrogen atom to which they are attached represent 1-pyrrolidinyl, 1-piperidinyl, 4-morpholinyl, 1-piperazinyl, 1-(4-methyl)-piperazinyl or 1-imadazolyl and $R_3$ represents hydrogen or methyl.

Particularly preferred compounds are those in which $R_1$ represents hydrogen, methyl, ethyl, isopropyl, 2-methoxyethyl, allyl, propargyl or cyclopropyl, $R_2$ represents hydrogen or methyl or $R_1$ and $R_2$ together with the nitrogen atom to which they are attached represent 1-pyrrolidinyl, 4-morpholinyl or 1-imidazolyl and $R_3$ represents hydrogen.

The most preferred compounds however are those in which $R_1$ represents hydrogen, ethyl, allyl or propargyl, $R_2$ represents hydrogen and $R_3$ represents hydrogen, and, in particular the compounds:

2-cyclopropylamino-4-formylamino-6-ethylamino-s-triazine, 2-cyclopropylamino-4-formylamino-6-allylamino-s-triazine, 2-cyclopropylamino-4-formylamino-6-propargylamino-s-triazine and 2-cyclopropylamino-4-formylamino-6-amino-s-triazine.

The compounds of the formula I are obtained by methods which are known per se, for example by (a) converting a 2-cyclopropylamino-4-formamidino-6-amino-s-triazine of the formula II

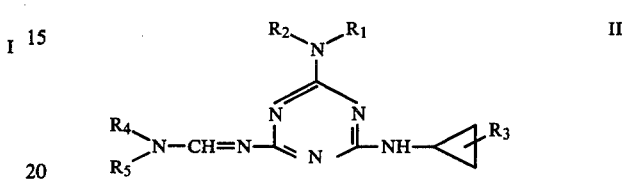

wherein $R_1$, $R_2$ and $R_3$ are as defined in formula I and $R_4$ and $R_5$ are the same or different and represent methyl or ethyl, into the corresponding 2-cyclopropylamino-4-formylamino-6-amino-s-triazine by hydrolysis, or (b) reacting a 2-cyclopropylamino-4,6-diamino-s-triazine of the formula III

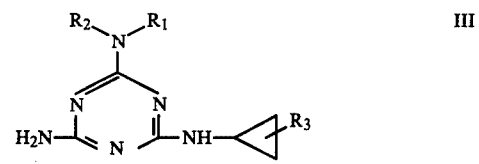

in which $R_3$ is as defined in formula I and in which $R_1$ and $R_2$ have the meanings assigned to $R_1$ and $R_2$ in formula I with the exception of hydrogen, with a formylating agent.

The hydrolysis (a) can be carried out with the addition of an acid, such as hydrochloric acid, at 0° to 100° C. under normal pressure. Advantageously, water is used as solvent or diluent, if appropriate with the addition of an organic solvent, such as dioxane, an alcohol, etc., whereupon the reaction product precipitates.

The reaction (b) is preferably carried out using formic acid and acetic anhydride as formylating reagent or by condensation of a compound of the formula III with an ortho-formate in the presence of catalytic amounts of a strong acid and subsequent partial hydrolysis. In the former case it is possible to use in the reaction a solvent or diluent which is inert to the reactants, and in the latter case the orthoester is used as solvent.

The starting material of the formula II can be obtained by reacting a triazine derivative of the formula III

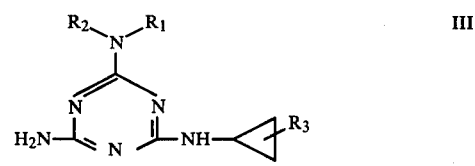

in which $R_1$, $R_2$ and $R_3$ are as defined in formula I, with an acetal of the formula V

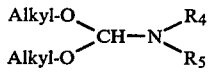

$$\text{V}$$

in which $R_4$ and $R_5$ have the meanings given in formula I.

The starting material of the formula III can be prepared by conventional methods from chlorine-substituted s-triazine derivatives by replacing chlorine with the corresponding amino group or groups.

Diamino- and triamino-s-triazines are described as chemosterilants for adult houseflies (*Musca domestica*) in U.S. Pat. No. 3,189,521. The chemosterilising action on insects of 2,4,6-triamino-s-triazine derivatives (melamine derivatives) is also described by S. Nagasawa et al., Botyu-Kagaku 39 (4), 105 (1974). A. B. Borkovec and A. B. DeMilo [J. Med. Chem. 10 (5), 457 (1967)] and G. C. LaBrecque, R. L. Fye, A. B. DeMilo and A. B. Borkovec [J. Econ. Entomol. 61, (6), 1621 (1968)] also describe the chemosterilising action of, among other compounds, 2-cyclohexylamino-4,6-diamino-s-triazine, 2-cyclohexylamino-4,6-dihexylamino-s-triazine and 2,4,6-tris-cyclohexylamino-s-triazine, and the salts thereof, on adult houseflies (*Musca domestica*). The chemosterilising action of acetylmelamines is described in U.S. Pat. No. 3,520,974.

The above mentioned insecticidal chemosterilants are employed to adult insects, i.e. the stage of reproduction and dissemination for impairing or preventing capability of producing offspring of said insects. Combatting populations of harmful insects by introduction of sterile insects capable of copulating into a normal insect population taking final aim at self-destruction represents an indirect method for combatting insects.

In practice, degeneration of an insect population by introduction of sterile insects into said population extends to a sequence of some to numerous generations of insects and therefore, further dissemination of organisms harmful to men or animals may occur by vector insects. Furtheron, insects may gradually become resistent to applied chemosterilants.

Therefore, direct methods for combatting insects by killing them or preventing individual development are required. Surprisingly, it has now been found that treating insect larvae representing the stage of eating and growing with compounds of formula I results in killing the freshly hatched larvae or preventing adults from hatching from the pupae. The mode of action of the compounds of formula I is not to be compared with that of classical insecticides, chemosterilants or juvenile hormone analogues.

The active compounds of the formula I can be used in particular for controlling hygiene pests and animal ectoparasites of the order Diptera and of the families: Culicidae, Simuliidae, Tipulidae, Muscidae and Calliphoridae.

The compounds of the formula I can be used as pure active substance or together with suitable carriers and/or additives. Suitable carriers and additives can be solid or liquid and correspond to the substances conventionally used in the art of formulation, for example natural or regenerated substances, solvents and/or dispersants.

The compositions according to the invention are manufactured in known manner by homogeneously mixing and/or grinding active substances (compounds) of the formula I with the suitable carriers, with or without the addition of dispersants or solvents which are inert to the active substances.

The active substances may be processed to the following formulations:

Solid formulations

Dusts, tracking agents and granules (coated granules, impregnated granules and homogeneous granules), premix (feed additive).

Liquid formulations (a) active substance concentrates which are dispersible in water: wettable powders, pastes and emulsions;
(b) solutions: sprays (aerosols).

To manufacture solid forms (dusts, tracking agents), the active substances are mixed with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used alone or in admixture with one another.

Granules can be very easily manufactured by dissolving an active substance of the formula I in an organic solvent and applying the solution thereby obtained to a granulated mineral, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation is carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having preferably a bulk density of 300 g/liter to 600 g/liter can also be manufactured with the aid of atomisers.

It is also possible to obtain granules by compacting the carrier with the active substance and additives and subsequently comminuting the product.

To these mixtures can also be added additives which stabilize the active substance and/or nonionics, anionics and cationics, which, for example, ensure a better wettability (wetting agents) and dispersibility (dispersants). Examples of suitable substances are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulphonic acid, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinylpyrrolidone, polyvinyl alcohol, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and anti-foams and, if appropriate, solvents.

Wettable powders and pastes are obtained by mixing and grinding the active substances with dispersants and pulverulent carriers in suitable devices until homogeneity is attained. Suitable carriers are, for example, those already mentioned for the solid forms of application. In some cases it is advantageous to use mixtures of different carriers. Examples of dispersants are: condensation products of sulphonated naphthalene and sulphonated naphthalene derivatives with formaldehyde, condensation products of naphthalene or naphthalene sulphonic acids with phenol and formaldehyde, as well as alkali metal, ammonium and alkaline earth metal salts of lignin sulphonic acid, in addition, alkylaryl sulphonates, alkali metal and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride and fatty acid alkali metal and alkaline earth metal salts.

Suitable anti-foams are for example silicone oils.

The active substances are so mixed, ground, sieved and strained with the additives mentioned above that, in wettable powders, the solid particle size of 0.02 to 0.04 mm and in pastes, of 0.03 mm, is not exceeded. Emulsifiable concentrates and pastes are manufactured by using dispersants, such as those referred to above, organic solvents, and water. Examples of suitable solvents are: alcohols, dimethyl sulphoxide, and mineral oil fractions which boil between 120° and 350° C. The solvents must be virtually odourless and inert to the active substances.

Furthermore, the compositions according to the invention can be applied in the form of solutions. For this purpose the active substance or several active substances of the general formula I are dissolved in suitable organic solvents or mixtures of solvents. Aliphatic and aromatic hydrocarbons, chlorinated derivatives thereof, alkylnaphthalenes and mineral oils, singly or in admixture, can be used as organic solvents.

Formulations of the novel active compounds of the formula I are described hereinafter. The parts denote parts by weight.

Dusts

The following substances are used to manufacture (a) a 0.5% and (b) a 2% dust:
(a) 0.5 part of active substance
99.5 parts of talc
2 parts of active substance
1 part of highly disperse silicic acid
97 parts of talc.
The active substances are mixed with the carriers and ground.

Tracking Agents 5 parts of active substance are mixed with
95 parts of carbonate of lime and ground to an average particle size of 80μ.

Granules 5 parts of active substance are dissolved in a solvent, e.g. methylene chloride, and mixed with
2 parts of polyethylene glycol ("Carbowax").
91.5 parts of calcium carbonate are impregnated with the mixture and
1.5 parts of precipitated silicic acid are admixed.
The solvent is subequently evaporated.

Wettable Powder 50 parts of active substance are mixed with
5 parts of a dispersing agent, e.g. sodium lignin sulphonate,
5 parts of a wetting agent, e.g. dibutylnaphthalene-sulphonic acid
10 parts of silicic acid and
30 parts of China clay and the mixture is finely ground.

Emulsifiable Concentrate 20 parts of active substance are mixed with
20 parts of emulsifier, e.g. a mixture of alkylarylpolyglycol ether with alkylarylsulphonates, and
60 parts of solvent until the solution is completely homogeneous. By diluting this concentrate with water it is possible to obtain an emulsion of the desired concentration.

Premix (feed additive)

0.25 part of active substance and
4.75 parts of secondary calcium phosphate, or China clay, aerosil or carbonate of lime are homogeneously mixed with
95 parts of an animal feed, e.g. poultry food.

Spray

The following constituents are used to manufacture a 2% spray:
2 parts of active substance
98 parts of kerosene.

Other biocidal active substances or agents can be admixed with the compositions described hereinabove. Thus in addition to the cited compounds of the general formula I, the compositions of the present invention can contain, for example, insecticides to broaden the activity spectrum.

The compositions, or the active compounds contained therein, exert their inhibitory action therefore chiefly on the development of larvae or pupae of insects, preferably of the order Diptera.

EXAMPLE 1

2-Cyclopropylamino-4-formylamino-6-morpholino-s-triazine 25 g of 2-cyclopropylamino-4-N',N'-dimethylformamidino-6-morpholino-s-triazine are dissolved in 1000 ml of water and the solution is treated with 100 ml of 1 N hydrochloric acid. After stirring for 15 minutes at room temperature, the 2-cyclopropylamino-4-formylamino-6-morpholino-s-triazine with a melting point of 288° C. begins to precipitate. The crude product is recristallised from dimethylformamide. Melting point: 291°–292° C.

The following compounds of the formula I are prepared in accordance with the above procedure:

| No. | Compound | mp. in °C. |
|---|---|---|
| 1 | 2-cyclopropylamino-4-formylamino-6-morpholino-s-triazinehydrochloride | 244–245 |
| 2 | 2-cyclopropylamino-4-formylamino-6-pyrrolidino-s-triazine | 260–261 |
| 3 | 2-cyclopropylamino-4-formylamino-6-methylamino-s-triazine | 244–245 |
| 4 | 2-cyclopropylamino-4-formylamino-6-ethylamino-s-triazine | 257–258 |
| 5 | 2-cyclopropylamino-4-formylamino-6-allylamino-s-triazine | 245–246 |
| 6 | 2-cyclopropylamino-4-formylamino-6-isopropylamino-s-triazine | 199–201 |
| 7 | 2-cyclopropylamino-4-formylamino-6-propargylamino-s-triazine | 258–260 |
| 8 | 2-cyclopropylamino-4-formylamino-6-imidazolo-s-triazine | 256–259 |
| 9 | 2-cyclopropylamino-4-formylamino-6-dimethylamino-s-triazine | 259–261 |
| 10 | 2-cyclopropylamino-4-formylamino-6-(2-methoxyethylamino)-s-triazine | 214–215 |
| 11 | 2,6-bis-(cyclopropylamino)-4-formylamino-s-triazine | 259–260 |
| 12 | 2-cyclopropylamino-4-formylamino-6-amino-s-triazine | 269–271 |
| 13 | 2-cyclopropylamino-4-formylamino-6-(N-methyl-N-ethylamino)-s-triazine | 205 |

EXAMPLE 2

Action against *Musca domestica*

50 g of freshly prepared CSMA nutrient substrate for maggots were charged into beakers. 2.5 ml portions of a 1% acetonic solution of the respective active substance were pipetted onto the nutrient substrate present in the beakers. The substrate was then thoroughly mixed and the solvent subsequently allowed to evaporate.

Then 25 one-, two- and three-day-old maggots and approx. 50 eggs of *Musca domestica* were put into each of the beakers containing the treated nutrient substrate for testing with each active substance. After the maggots had pupated, the pupae were separated from the substrate by flushing them out with water and counted. The number of flies which had hatched out of the pupae was then counted after 10 days and any influence on the metamorphosis thereby determined.

In the above text, the compounds of Example 1 displayed a good action against *Musca domestica*.

EXAMPLE 3

Action against *Lucilia sericata*

1 ml of an aqueous solution containing 0.5% of active substance was added to 9 ml of a culture medium at 50° C. Then approx. 30 freshly hatched larvae of *Lucilia sericata* were added to the culture medium and the insecticidal action was determined by evaluation of mortality after 48 and 96 hours respectively.

In this test, the compounds of the formula I acted well against *Lucilia sericata*.

EXAMPLE 4

Action against *Aëdes aegypti* larvae

Active substance concentrations of 10, 5 and 1 ppm respectively were obtained by pipetting a specific amount of a 0.1% solution of the active substance in acetone onto the surface of 150 ml of water in each of a number of beakers.

After the acetone had evaporated, 30 to 40 two-day-old larvae of *Aëdes aegypti* were put into each of the beakers containing the active substance solution. Evaluation of mortality is made after 1, 2 and 5 days respectively.

In this test, the compounds of the formula I acted well against *Aëdes aegypti*.

What we claim is:

1. A compound of the formula

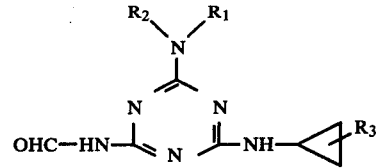

wherein
R₁ represents hydrogen, C₁–C₄-alkyl which is unsubstituted or substituted by lower alkoxy, or represents C₃–C₄-alkenyl, C₃–C₄-alkynyl, cyclopropyl, hydroxy, methoxy or ethoxy,
R₂ represents hydrogen, methyl or ethyl, or
R₁ and R₂ together with the nitrogen atom to which they are attached represent a 5- or 6-membered heterocyclic ring which can contain a further nitrogen atom or an oxygen atom, and
R₃ represents hydrogen or methyl,
and the acid addition salts thereof.

2. The compound according to claim 1 wherein R₁ represents hydrogen, C₁–C₄-alkyl which is unsubstituted or substituted by lower alkoxy, or represents C₃–C₄-alkenyl, C₃–C₄-alkynyl, cyclopropyl, hydroxyl, methoxy or ethoxy, R₂ represents hydrogen, methyl or ethyl, or R₁ and R₂ together with the nitrogen atom to which they are attached represent 1-pyrrolidinyl, 1-piperidinyl, 4-morpholinyl, 1-piperazinyl, 1-(4-methyl)-piperazinyl or 1-imadazolyl and R₃ represents hydrogen or methyl and the acid addition salts thereof.

3. The compound according to claim 1 wherein R₁ represents hydrogen, methyl, ethyl, isopropyl, 2-methoxyethyl, allyl, propargyl or cyclopropyl, R₂ represents hydrogen or methyl or R₁ and R₂ together with the nitrogen atom to which they are attached represents 1-pyrrolidinyl, 4-morpholinyl or 1-imidazolyl and R₃ represents hydrogen and the hydrochlorides thereof.

4. The compound according to claim 1 wherein R₁ represents hydrogen, ethyl, allyl or propargyl, R₂ represents hydrogen and R₃ represents hydrogen.

5. 2-Cyclopropylamino-4-formylamino-6-ethylamino-s-triazine according to claim 1.

6. 2-Cyclopropylamino-4-formylamino-6-allylamino-s-triazine according to claim 1.

7. 2-Cyclopropylamino-4-formylamino-6-propargylamino-s-triazine according to claim 1.

8. 2-Cyclopropylamino-4-formylamino-6-amino-s-triazine according to claim 1.

9. A pesticidal composition which comprises an effective pesticidal amount of a compound of claim 1 together with a suitable carrier or additive or mixtures thereof.

10. A method for combatting insects which comprises applying to their developmental stages an insecticidally effective amount of a compound of the formula I of claim 1.

11. The method according to claim 10 for combatting insects in their larval or pupal stage in sufficient amount to inhibit metamorphosis.

12. The method according to claim 11 for combatting insects of the order Diptera.

13. The method according to claim 12 for combatting insects of the families Culicidae, Simuliidae, Tipulidae, Muscidae and Calliphoridae which belong to the order Diptera.

* * * * *